(12) United States Patent
Bray et al.

(10) Patent No.: US 7,089,795 B2
(45) Date of Patent: Aug. 15, 2006

(54) ULTRASONIC CHARACTERIZATION OF POLYMERIC CONTAINERS

(76) Inventors: Don E. Bray, P.O. Box 10315, College Station, TX (US) 77842-0315; Raed Al-Zubi, P.O. Box 80, French Camp, CA (US) 95231

( * ) Notice: Subject to any disclaimer, the term of this patent is extended or adjusted under 35 U.S.C. 154(b) by 0 days.

(21) Appl. No.: 10/679,658

(22) Filed: Oct. 6, 2003

(65) Prior Publication Data

US 2005/0072235 A1    Apr. 7, 2005

(51) Int. Cl.
*G01N 29/07*    (2006.01)
(52) U.S. Cl. .............................. 73/598; 73/622; 73/644
(58) Field of Classification Search .......... 73/597–598, 73/644, 622
See application file for complete search history.

(56) References Cited

U.S. PATENT DOCUMENTS

| | | | | |
|---|---|---|---|---|
| 4,160,385 A | * | 7/1979 | Gromlich et al. ............. | 73/622 |
| 4,386,527 A | * | 6/1983 | Maucher ...................... | 73/597 |
| 4,458,534 A | * | 7/1984 | Kising ......................... | 73/644 |
| 4,567,747 A | * | 2/1986 | Matay .......................... | 73/597 |
| 4,680,966 A | * | 7/1987 | Nicolas ........................ | 73/597 |
| 5,507,183 A | * | 4/1996 | Larue et al. .................. | 73/598 |
| 5,608,165 A | * | 3/1997 | Mozurkewich, Jr. ......... | 73/599 |
| 5,661,243 A | * | 8/1997 | Bryan et al. .................. | 73/598 |
| 6,578,424 B1 | * | 6/2003 | Ziola et al. ................... | 73/644 |

FOREIGN PATENT DOCUMENTS

| | | | | |
|---|---|---|---|---|
| JP | 61096405 A | * | 5/1986 | |
| JP | 63250562 A | * | 10/1988 | |
| JP | 279856 | * | 12/1991 | |

OTHER PUBLICATIONS

Translation of JP-279856.*

* cited by examiner

*Primary Examiner*—Hezron Williams
*Assistant Examiner*—Nashmiya Fayyaz
(74) *Attorney, Agent, or Firm*—David W. Carstens; Carstens & Cahoon, LLP

(57) ABSTRACT

The present invention provides a system and method for detecting changes in the properties of a polymeric material. A frame is hand held against the outside surface of a curved polymeric test specimen, e.g., fluid tank. A transmitting probe attached to the frame emits critically refracted ultrasonic waves that travel longitudinally across the chord of said curved test specimen and are detected by at least one receiving probe attached to the frame. A data processing system measures the travel time of the ultrasonic waves from the transmitting probe to the receiving probe and compares this measured travel time to an expected travel time. Variations in material properties along the penetration path of the ultrasonic waves can be detected from deviation in the measure travel time of the waves from the expected control values. Measuring the temperature of the polymeric specimen allows adjustment of the measured travel time of the waves to account for temperature effects on the polymeric material. Information about the contents of the container is used to further adjust the travel time of the ultrasonic waves to account for mechanical stress effects on the polymeric container walls.

10 Claims, 11 Drawing Sheets

FIG. 5B ive testing of mechanical properties within solid materials using the $L_{CR}$ ultrasonic tech-
ULTRASONIC CHARACTERIZATION OF POLYMERIC CONTAINERS

BACKGROUND OF THE INVENTION

1. Technical Field

The present invention relates generally to an apparatus and method for non-destructnique. Specifically, the present invention relates to an improved technique and apparatus that provides a more accurate measurement of degradation in polymeric rotational molded components such as pressure vessels, tanks and piping.

2. Description of Related Art

The non-destructive testing for stress in materials has long been recognized as an important method for evaluating structural components to predict both the failure location and rate, to identify stressed components prior to failure, and many other safety related considerations. Non-destructive testing is used extensively in a wide variety of industries including the aviation, automotive, petroleum, and chemical industries, and various construction and structural related fields. The use of non-destructive testing on specific components ranges from the testing of polymeric and metal piping and pressure vessels for loss of wall as well as for fatigue cracks. Additionally, steel turbine blades in jet engines, steel support beams in bridges, and other large structures are monitored by nondestructive testing. Components in use can be tested to determine the stress levels in the components without damaging or destroying the components. The benefit of non-destructive testing is self-evident.

In polymeric materials, mechanical properties may change with time. The changes may be due to environmental effects caused by ultraviolet exposure, the chemical environment of the surrounding air as well as the commodity contained in the tank. Laboratory studies of samples held under UV light for extended periods of time show that there is a correlation between the level of degradation of a rotational molded polyethylene tank and its ultrasonic characteristics, namely velocity and attenuation. This correlation is measurable and quantifiable. Based on these findings, field trials were conducted on a number of in-service rotational molded cross-linked polyethylene tanks at different sites, for both industrial and fertilizer storage applications. These tanks varied in their service life from present year production to more than fifteen years of service. The ultrasonic wave characteristics from the field tasks were in line with the lab observations. These results indicate that the level of overall degradation of the tank may be quantified based on the measured relevant ultrasonic data.

Since the mechanical properties affect the likelihood of failure, a convenient and reliable nondestructive technique for evaluating the mechanical properties of polymer tanks in service would be useful to industry. Ultrasonic properties such as speed, attenuation, and frequency characteristics are directly related to the mechanical properties of the material. A newly designed apparatus using ultrasonic $L_{CR}$ waves excited and received on the outer curved surfaces of rotational molded polymeric tanks will enable the inspection of tanks in the field.

SUMMARY OF THE INVENTION

The present invention provides a system and method for detecting changes in the properties of a polymeric material. A frame is hand held against the outside surface of a curved polymeric test specimen, e.g., fluid tank. A transmitting probe attached to the frame emits critically refracted ultrasonic waves that travel longitudinally across the chord of said curved test specimen and are detected by at least one receiving probe attached to the frame. A data processing system measures the travel time of the ultrasonic waves from the transmitting probe to the receiving probe and compares this measured travel time to an expected travel time. Variations in material properties along the penetration path of the ultrasonic waves can be detected from deviation in the measure travel time of the waves from the expected control values.

Thermocouples may also be attached to the hand held frame to measure the temperature of the polymeric specimen, which allows adjustment of the expected velocity of the waves to account for temperature effects on the polymeric material. Information about the contents of the container is used to further adjust the velocity of the ultrasonic waves to account for mechanical stress effects on the polymeric container walls.

BRIEF DESCRIPTION OF THE DRAWINGS

The novel features believed characteristic of the invention are set forth in the appended claims. The invention itself, however, as well as a preferred mode of use, further objectives and advantages thereof, will best be understood by reference to the following detailed description of an illustrative embodiment when read in conjunction with the accompanying drawings, wherein:

FIG. 5B shows the GUI set-up panel with the contents of the tank type pull-down menu;

DETAILED DESCRIPTION OF THE INVENTION

The present invention provides an inspection method for evaluating the remaining service life of rotational molded polyethylene tanks used in the storage of high-end chemicals and fertilizers. It has been well known for some time that exposure to ultraviolet radiation changes the mechanical properties of polyethylene material. Ultrasonic wave speeds are directly related to mechanical properties, making them suitable for measuring the mechanical properties of these tanks in service.

Ultrasonic devices for determining the mechanical properties of polymers include the work of McKinley et al (U.S. Pat. No. 5,408,882, Apr. 25, 1995) where they incorporate a wedge shaped focuser made of polymethylmethacrolate to match the impedance of the exciter to that of the receiving composite material. Using this, they excite a substantially longitudinal wave from the sender to the receiver. Properties of the material in various directions are obtained by rotating the transducer about a vertical line perpendicular to the surface. The frequency of the excited wave is varied by selecting different probe frequencies for the sender and receiver probes, where the sending and receiving transducers are substantially matched. Kline (U.S. Pat. No. 5,127,268, Jul. 7, 1992) describes an ultrasonic method for determining fiber volume fraction using measured longitudinal and shear waves in composite materials composed of at least two different constituent materials. Antich et al. (U.S. Pat. No. 5,038,787, Jul. 13, 1991, U.S. Pat. No. 5,197,475, Mar. 30, 1993) use ultrasonics methods to evaluate material properties where they vary the angle of the incident and receiving transducer and analyze the amplitude of the received signal. Dixon (U.S. Pat. No. 3,720,098, Mar. 13, 1973) uses simultaneously generated longitudinal and shear waves to measure physical properties of material. Neiters et al. (U.S. Pat. No. 5,631,424, May 20, 1997) describe a method for ultrasonic evaluation and detection of features in polycrystalline materials. Bussiere et al. (U.S. Pat. No. 4,790,188, Dec. 13, 1988) present a method for launching ultrasonic waves used for evaluating the formability of solid plate. Bray (U.S. Pat. No. 6,523,418, Feb. 25, 2003, U.S. Pat. No. 6,477,473, Nov. 05, 2002, U.S. Pat. No. 6,424,922 B1, Jul. 23, 2202) presents an ultrasonic probe and method used for stress measurement where a measured amount of force at the interface and wedges which rotate relative to the surface of the curved or flat material being inspected maintain constant contact point separation. DeLacy (U.S. Pat. No. 4,494,408, Jan. 22, 1985) shows a method where acoustic emissions are used to detect undesirable residual stresses in composite materials. The sounds emitted as transformations occur and picked up by the system are correlated with residual stresses in the composite.

Figure 1:
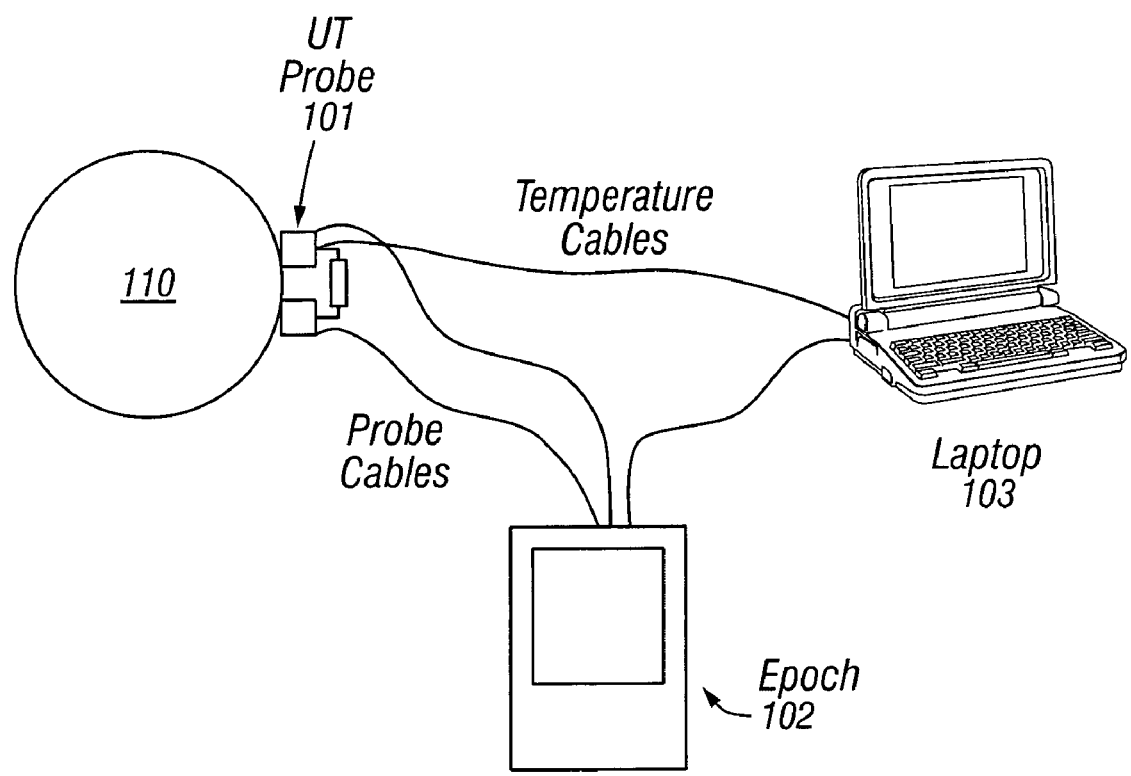
FIG. 1 shows a typical setup used for the field testing rotational molded polyethylene tanks in accordance with the present invention.

FIG. 1 shows the typical setup used for the field tests in accordance with the present invention. A probe assembly 101 containing send/receive ultrasonic transducers, as well as thermocouples, is held against the surface of a tank 110. An Epoch 4 102 is used as the ultrasonic unit. It obtains the ultrasonic results from the probe assembly 101 and transmits them to a (laptop) computer 103. Thermocouple readings for temperature go directly to a PCMIA card on the laptop 103.

Figure 2A:
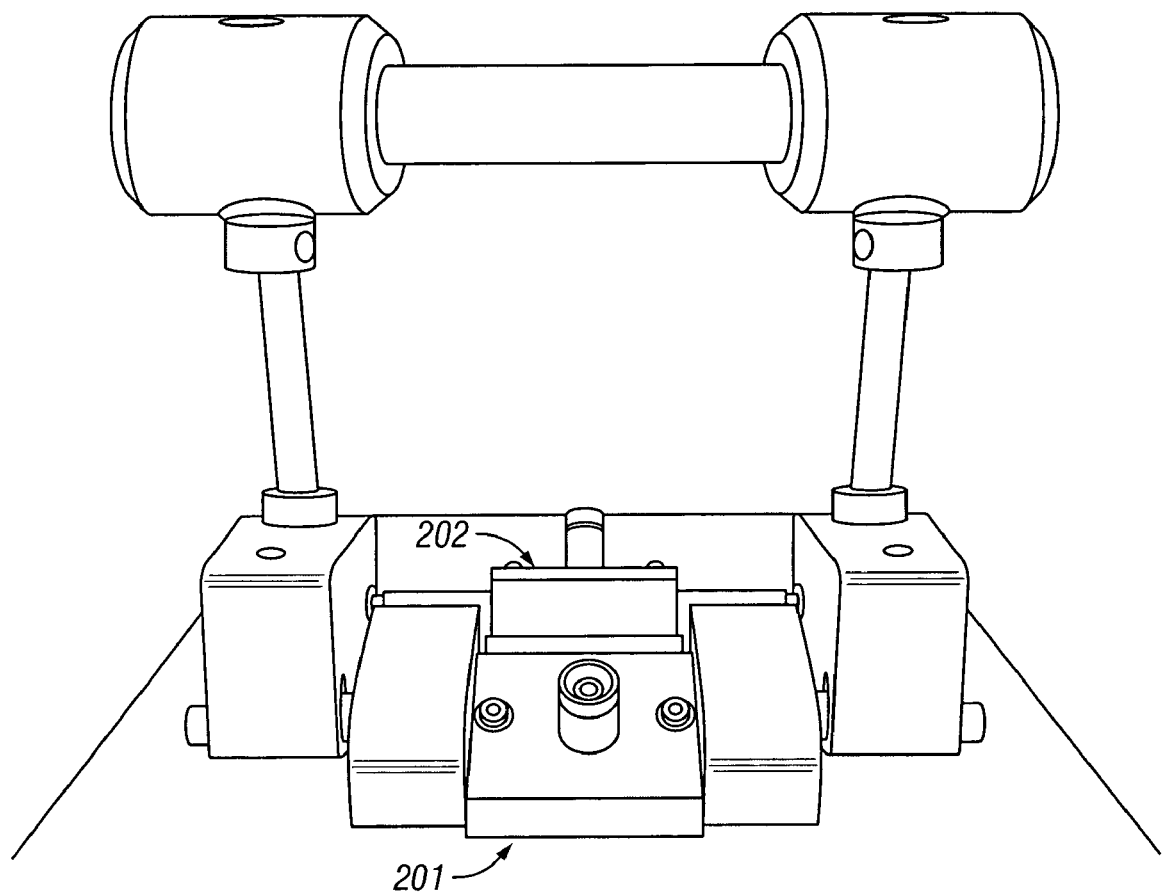
FIG. 2A shows the front view of the hand-held probe assembly containing the send and receive ultrasonic transducers.
Figure 2B:
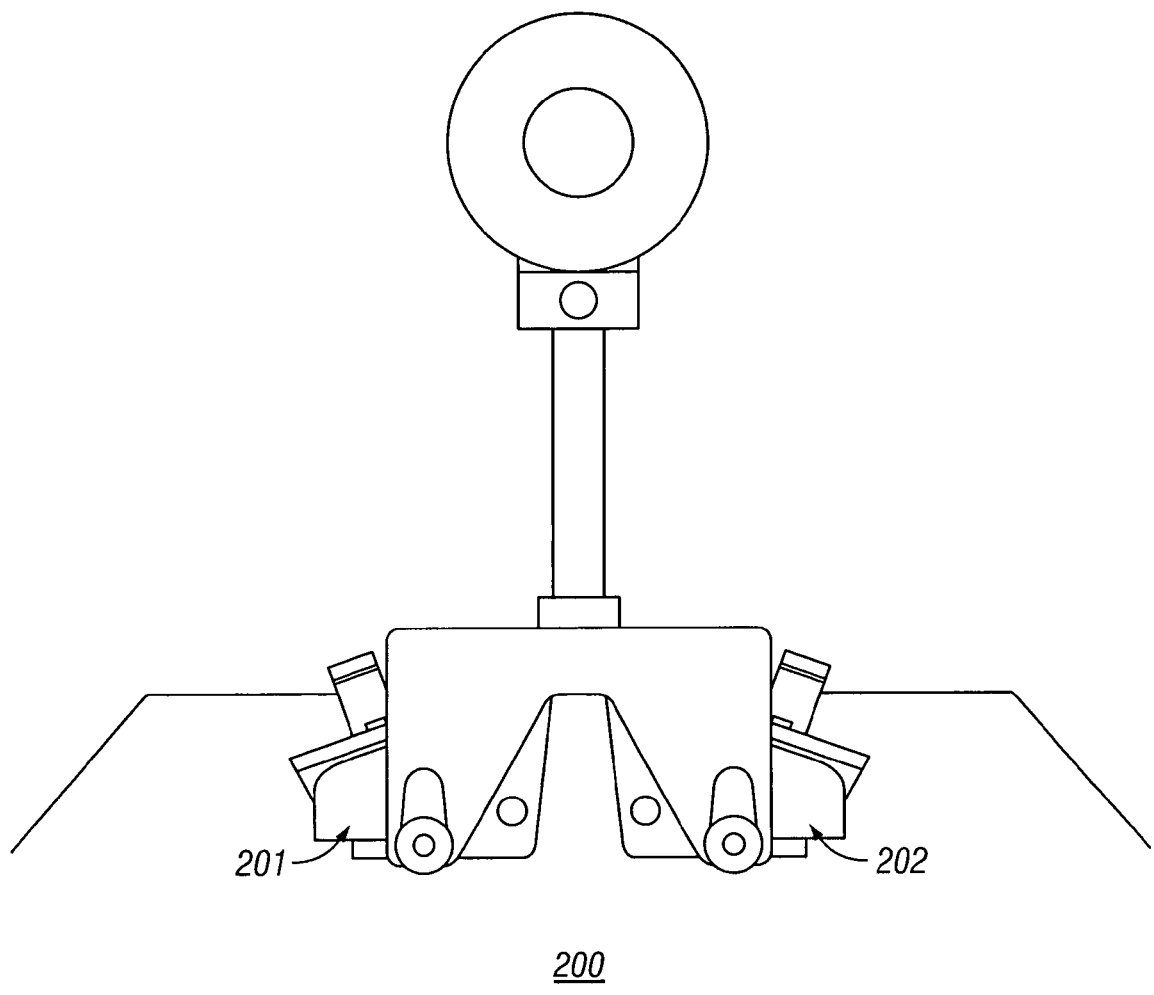
FIG. 2B shows a side view of the probe assembly.

FIG. 2A shows the front view of the hand-held probe assembly containing the send and receive ultrasonic transducers. FIG. 2B shows a side view of the probe assembly. The send/receive transducers are located in rotatable, wedge-shaped probes 201, 202 that allow the probe assembly 200 to be tangentially coupled against the surface of a curved test specimen and properly oriented to send and receive the wave pulse across the chord length of the curved test specimen. The ability of the probes 201, 202 to rotate freely tangential to the contact point allows for the probe assembly 200 to be properly held against myriad curved engineering components with various diameters and angular arcs. The more degrees of freedom (mobility) the probes 201, 202 have, the better the signal. In addition, greater mobility of the probes 201, 202 will increase the comfort to the human user and improve the usability. The probe assembly 200 is flexible, enabling testing on tanks with different diameters. Probe spacing can be adjusted to accommodate closer spacing required for older tanks having a large amount of amplitude loss in the signal propagating in the tank (attenuation).

Figure 3:
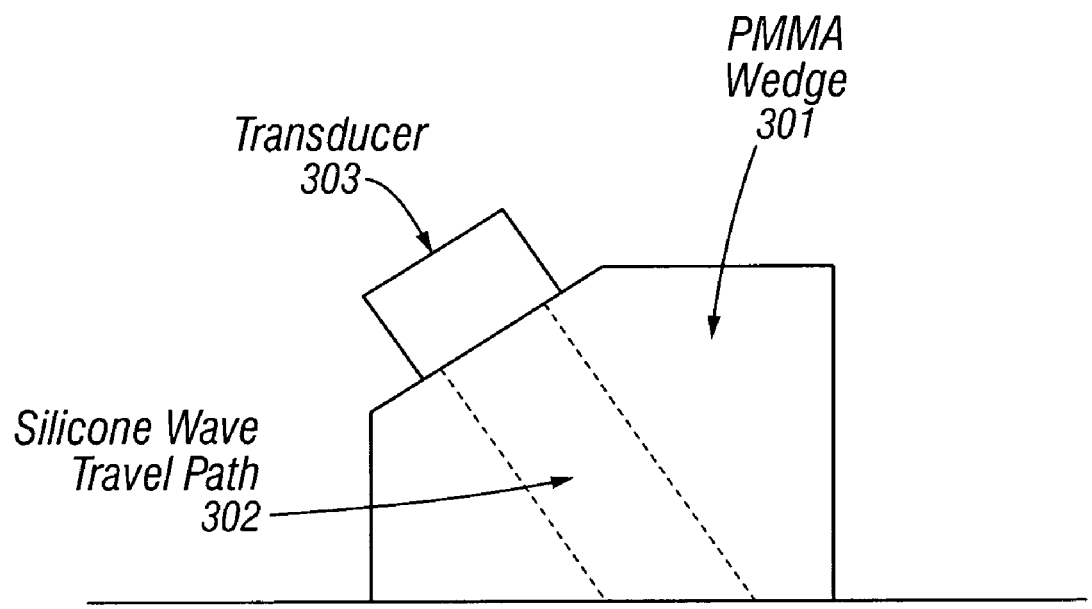
FIG. 3 shows the internal structure of the sending and receiving probes.

FIG. 3 shows the internal structure of the sending and receiving probes. Each probe comprises three main components: a Poly-methyl-methacrylate (PMMA) wedge 301, a silicone wave travel path 302, and a transducer 303. The distinct advantages of $L_{CR}$ ultrasonic technique used by the apparatus described here is that the use of the low speed silicone enables excitation of the $L_{CR}$ wave in the polymer and the flexibility of the rotating wedges gives repeatable velocity measurements using hand held application. Lexan wearfaces can be used at the probe tank interface to increase the life of the probes. Use of higher frequency source probes coupled with suitably selected lower frequency receiver probes maximizes the signal strength. The velocities calculated from the travel-time enable accurate determination tank material condition.

The probe assembly containing the wedges is hand held against the tank. A standard ultrasonic couplant is used between the probes and the tank. As explained above, the rotating wedges are free to give a more uniform contact area between the probes and the tank. Probe pivot points are above the contact (entry) point of the probes. True travel distance of the $L_{CR}$ wave is determined in an algorithm based on the distance of the pivot point above the contact point, the probe spacing, and the tank diameter. This feature enables the reliable and repeatable measurement of 2% or better on the $L_{CR}$ travel-time changes.

Generally speaking, the requirement for the contact area during the inspection is that it must be free of dirt, water, oil, scale and other loose debris that can affect the probe contact. Ordinary scale that is tightly adhered to the surface does not affect the $L_{CR}$ data, provided that it is smooth. Ultrasonic instrumentation required for collecting $L_{CR}$ data is a typical commercial ultrasonic flaw detector or thickness measurement instrument capable of a travel time resolution of 10 ns or better and able to send the signal information to the laptop hosting the data entry software and screen. Specially designed executable files based on Labview are preferable for data interpretation. Judgment of material degradation would be based on the deviation of the observed velocity from the previously new tank norm (described in more detail below).

Figure 4:
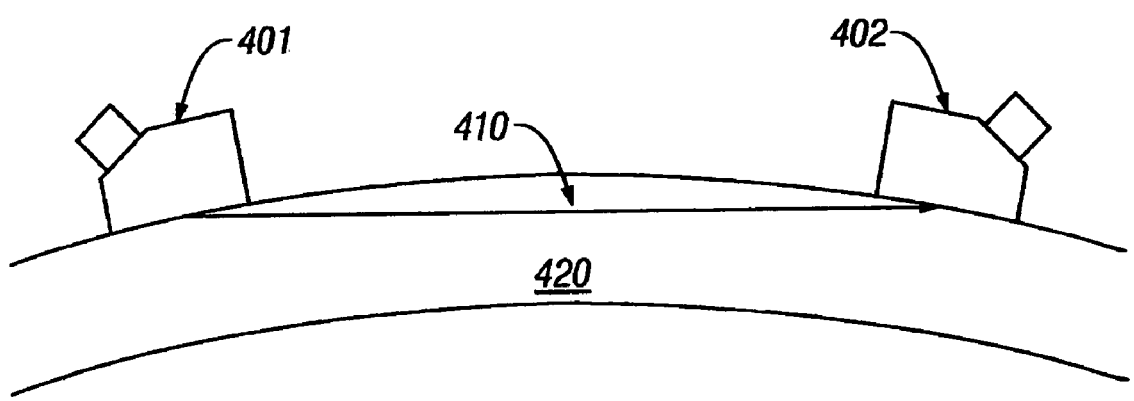
FIG. 4 illustrates the propagation of a $L_{CR}$ longitudinal wave through a curved test material.

FIG. 4 illustrates the propagation of a $L_{CR}$ longitudinal wave through a curved test material. The new feature of the $L_{CR}$ technique is the ability to excite and detect a longitudinal wave 410 travelling across the chord of a curved surface 420, in the longitudinal direction and at various distances between probe locations. Analysis of the results produces an accurate measure of the polymer velocity in the tank wall. The $L_{CR}$ probe assembly operates in a send-receive mode, using one transmitter 401 and either one or more receivers 402. Both the send and receiving probes 401, 402 are on the outer surface of the material 420. The waves 410 may be excited and received using a variety of transduction techniques including piezoelectric, phased-array or laser or other suitable method. Hybrid systems may use combinations of those methods for transduction.

The $L_{CR}$ wave 410 is excited at approximately the first critical angle +/−2 degrees for the wedge and material combination. As the pulse 410 travels from the transmitter 401 to the receiver 402 as a bulk critically refracted longitudinal wave it encounters the material degradation and other effects in its path. Since the $L_{CR}$ wave propagation is just beneath the surface, the material property variations within its penetration path affect the speed. Surface conditions have little effect on the wave travel. The incident and receiving wave paths in the probe wedges are silicone columns, as illustrated in FIG. 3. The low speed of the silicone provides the correct wave speed combination enabling the excitation of $L_{CR}$ waves in the higher speed polymer materials.

Probe frequency must be properly chosen in order to maximize the energy of propagation in the polyethylene and to reduce the guided wave effects. Polyethylene is a very attenuative material, and wave propagation in these materials is better at lower frequencies. Too low of a frequency, however, will lead to guided waves which might be difficult to interpret. Frequencies of 0.5 MHz, 1.0 MHz and 2.25 MHz were selected for trial. Of the various combinations tested, a 2.25 MHz for the sender and 1.0 MHz for the receiver give the best performance.

As stated above, the spacing of the send/receive probes is adjustable. For example, probe spacing of 47 mm, 62 mm and 99 mm may be used. For most tanks, 47 mm is a suitable choice. Since attenuation increases with age, the probe frequency and spacing can be changed depending on the age of the test specimen. Generally, aged tanks require closer spacing and lower probe frequencies.

The send/receive probe combination for polymer tank inspection uses a high frequency probe as the sender and a specially chosen lower frequency probe as the receiver. This combination recognizes the pulse distortion that occurs in the material as the $L_{CR}$ signal propagates. The received pulse will show a reduced peak frequency as well as significant losses in the upper frequencies in the spectrum. The high/low frequency send/receive combination accommodates this behavior and enhances the inspection process. The signal is excited and received with a conventional, commercially available flaw detector capable of communication with a computer, e.g., a Panametrics Epoch 4 is a suitable instrument. Signal arrival times as well other waveform characteristics are communicated to the computer for analysis.

Ultrasonic investigations can reveal a variety of things about materials. Although the more common application is for flaw detection, there are a number of other anomalies that can be revealed by ultrasonics. Typical ultrasonic parameters used are velocity, attenuation, and frequency dispersion. In some instance, only one parameter is needed to classify a material condition. In other cases, two or more parameters are needed.

When measuring ultrasonic velocity, it is necessary to know exactly the travel path and time of the wave in the tank. The curvature of the tank and rotation movement of the probe requires that corrections be applied to the probe spacing to obtain the true travel distance. The corrected travel path distance is given by $$d_c = \frac{S_p}{\left(1 + \frac{2 \cdot h}{d_t \cdot 304.8}\right)}$$

where
$d_c$=corrected travel distance
$S_p$=probe spacing (mm)
$d_t$=tank diameter (feet)
h=height of probe rotation point above contact surface (10 mm for present probe)

304.8=units conversion

The travel-time measured by the Epoch 4 unit will be the overall time value, i.e. from the time the wave starts at the sending transducer to the time that it arrives at the receiving transducer. This obviously includes time in the silicone column, which is subtracted to give the true travel time in the tank wall. While this time in the silicone may be estimated, it can be easily accommodated by shifting the starting point for the Epoch unit so that the amount of time displayed on the screen is the true time in the tank wall. This is accomplished by calibration on a new, un-aged, sample and using the ZERO OFFSET to adjust the arrival time of the signal to give the expected velocity.

The arrival times are used to calculate a velocity for the particular probe spacing. Temperature and stress also affect the velocity of the signal traveling through the polymer. To accommodate the temperature dependent wave speed change, the temperature in the polymer material is measured at the probe with a temperature sensor. This temperature is transmitted to the computer and appropriate correction factors are included in the velocity calculation. Further, wall stress due to the commodity contained in the tank is determined from the height of the commodity and the location of the probe, since the pressure exerted by liquids against the side of the tank increases exponentially with the depth of the liquid (i.e. disproportionately greater pressure near the bottom than at the top). This stress effect is included in the final velocity calculation. Moreover, frequency variation and other analysis techniques may establish property gradients below the surface.

A computer algorithm incorporates the tank diameter, the travel time of the wave in the tank wall, the probe spacing, the temperature, and height and type of commodity in the tank to calculate a corrected velocity. The program for this work is specifically developed as an executable LabView file.

The measured velocity is compared to an expected value based on temperature measurements.

$$\Delta V = V_m - V_e$$

where $V_m$ is the measured velocity and $V_e$ is the expected velocity in new material based on the measured temperature. This difference between expected and measured velocity is used to estimate the mechanical properties in the tank wall.

The measured velocity is calculated from the travel time and corrected travel distance according to the equation $$V_m = \frac{d_c}{(t_{travel} - t_{si})} \cdot 1000$$

where
$d_c$=corrected travel distance
$t_{travel}$=measured travel time
$t_{si}$=temperature corrected travel time in Silicon wedges, and
1000=units conversion factor Measured polymer velocities range from approximately 2230 m/s for new polymer tanks, to 2350 m/s and above for those that have been in the field for 25 years or more.

Expected velocities are based on controlled, laboratory-established variations with temperature for the polymer materials. For example, the polyethylene samples in Table 1 were measured at room temperature.

TABLE 1

Summary of Longitudinal Wave Speeds for New Polyethylene Samples at 70°

| Sample | | Cl m/s |
|---|---|---|
| Linear Natural | LN | 2260 |
| Cross Linked Natural | CLN | 2230 |
| Linear Green | LG | 2220 |
| Cross Linked Black | CLB | 2210 |

At freezing temperatures velocities around 2400 m/s will be found in these new samples. At higher temperatures, the velocity decreases so that 2100 m/s speeds can be expected from new samples at 95° F. These expected temperature changes are incorporated into the computer program.

Figure 5A:
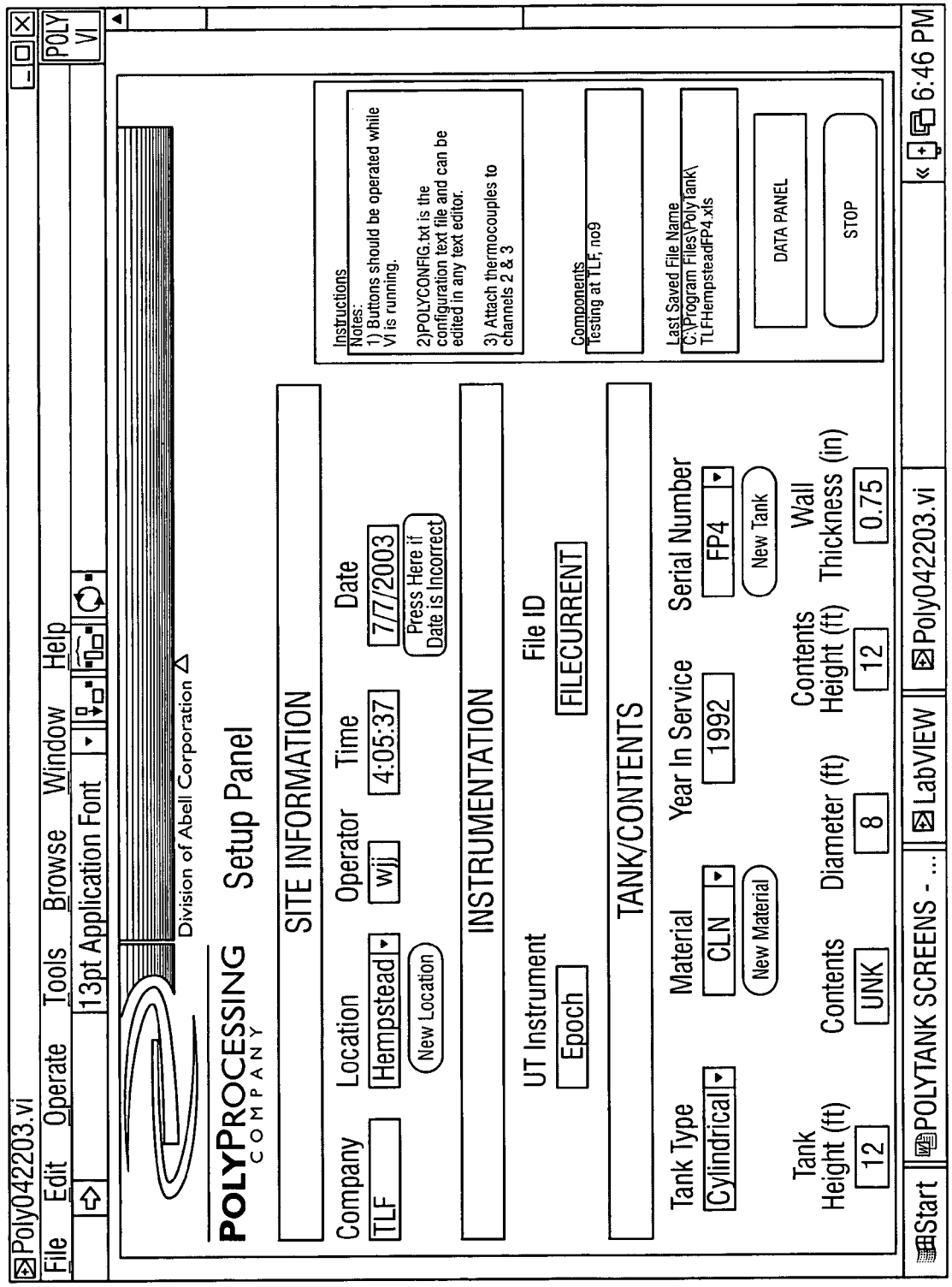
FIG. 5A shows a graphic user interface (GUI) set-up panel used to collect ultrasonic data for determining the physical properties of storage tanks.

FIG. 5A shows a graphic user interface (GUI) set-up panel used to collect ultrasonic data for determining the physical properties of storage tanks. The setup panel 500 is the first panel shown when the program is started and allows the user to enter data regarding the particular test set. The user is expected to enter information regarding the site, instrument and subject tank: the company and inspection site, the time and date as well as the operator, the type of ultrasonic instrument, the name of the stored file, the tank type, material and serial number, years in service, wall thickness, diameter, height, contents and contents height.

Keyboard inputs require the user to type the entry using the keyboard. Menu inputs allow the user to select a choice from the pull-down menu. Data fields are automatically entered by the software when a button is pressed and require no action from the user. Calculations are performed by the software and do not require action from the user.

Figure 5B:
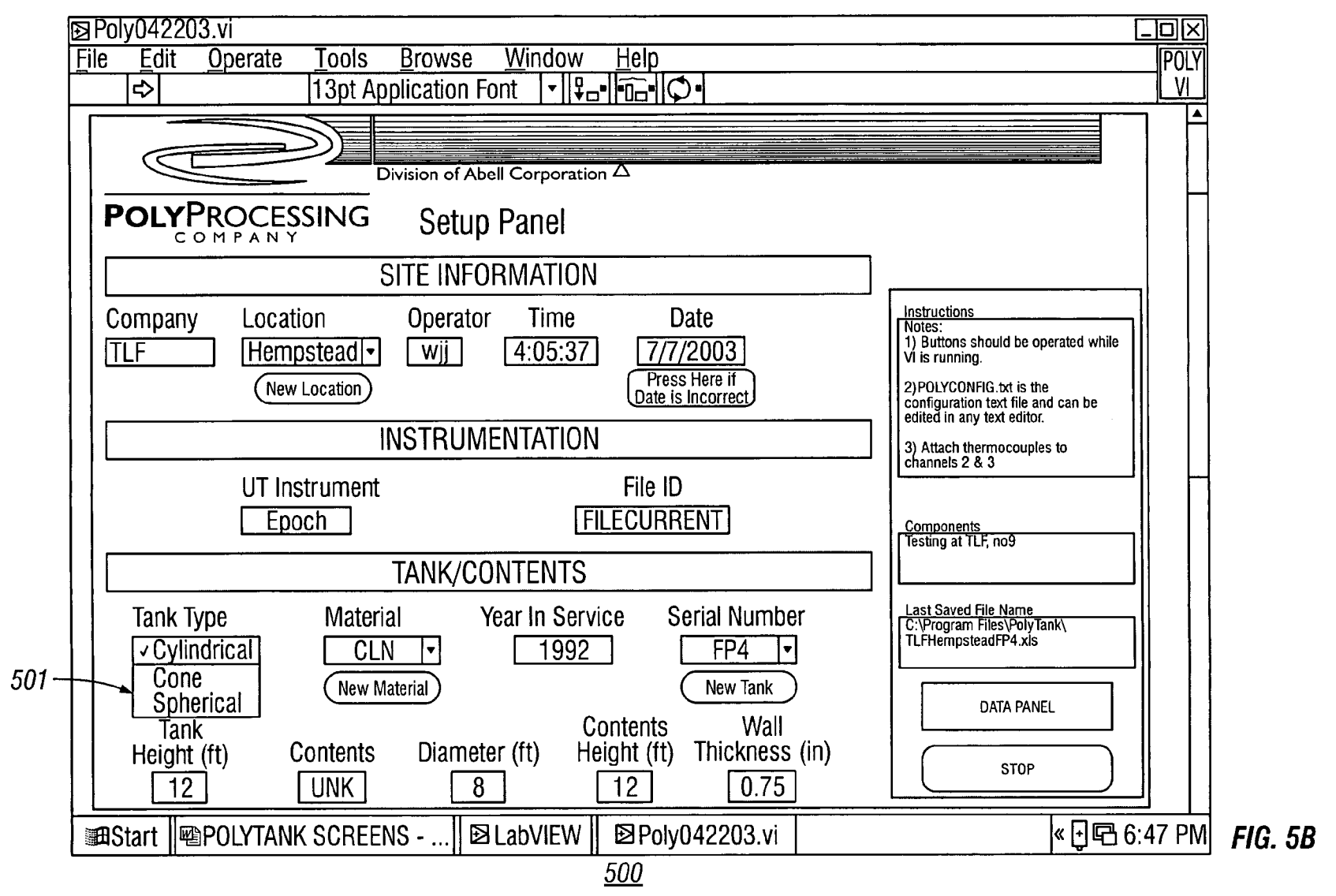

FIG. 5B shows the GUI set-up panel 500 with the contents of the tank type pull-down menu 501. The shape of the tank being tested will change the calculations to account for factors such as internal stress from the contents of the tank.

Figure 5C:
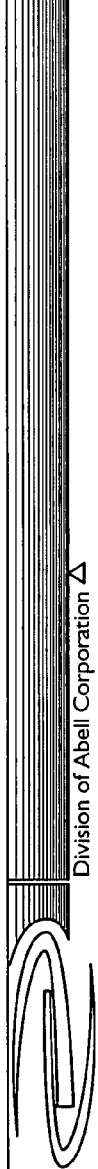
FIG. 5C shows the GUI set-up panel with the contents of the pull-down menu for the type of material comprising the tank.

FIG. 5C shows the GUI set-up panel 500 with the contents of the pull-down menu 502 for the type of material comprising the tank. As noted above, each type of polymeric material has a unique relationship between wave speed and temperature.

Figure 6A:
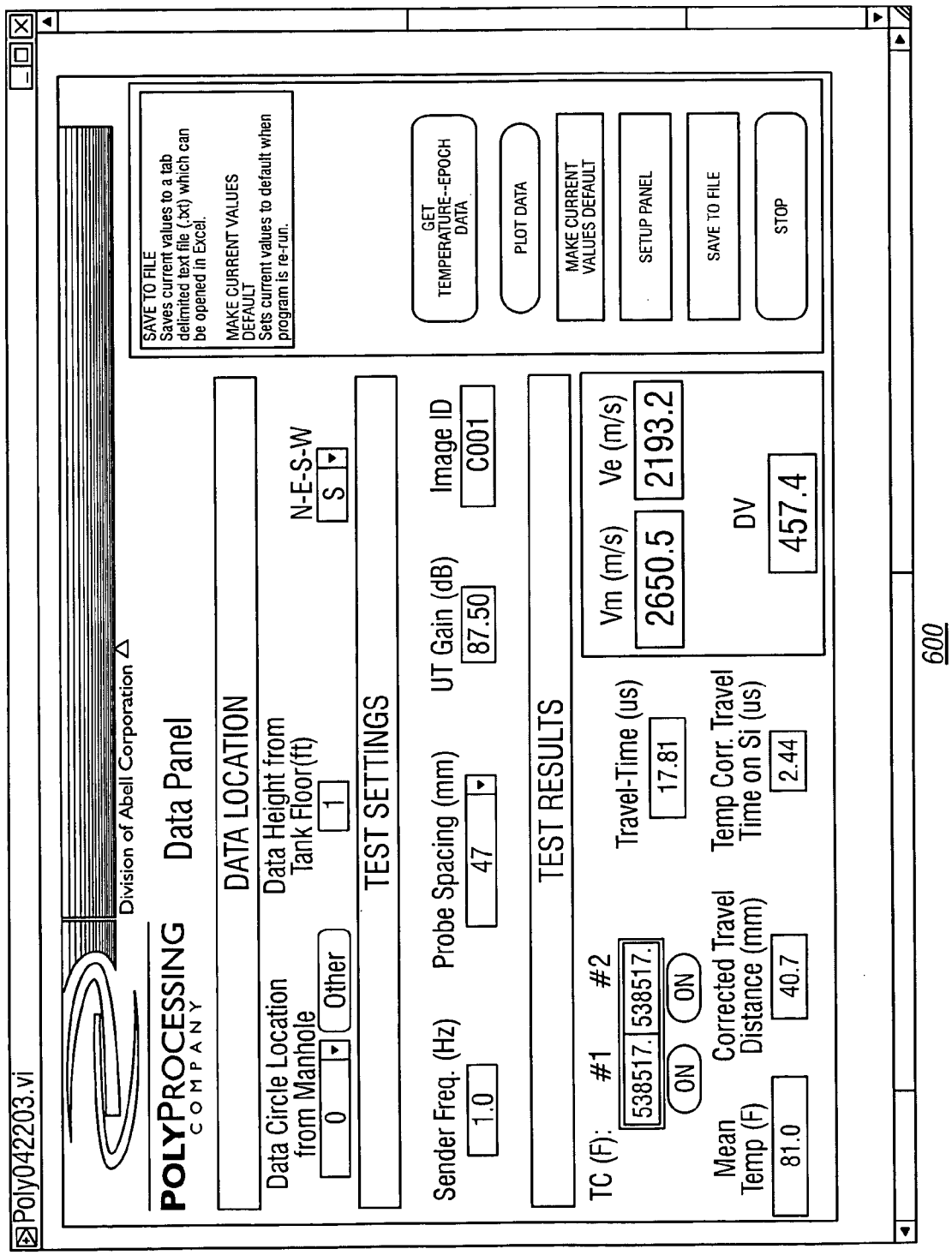
FIG. 6A shows a GUI data panel used to enter additional information regarding the specific tank tests and present the current test results.

FIG. 6A shows a GUI data panel used to enter additional information regarding the specific tank tests and present the current test results. The data panel 600 includes input for the circumferential and vertical location of the data point as well as north, east, south and west (NESW) orientation of the data point, which is required to determine the amount of sunlight reaching the data point area. Also included are the sender and receiver frequency combination, the probe spacing and the gain setting of the ultrasonic instrument.

Figure 6B:
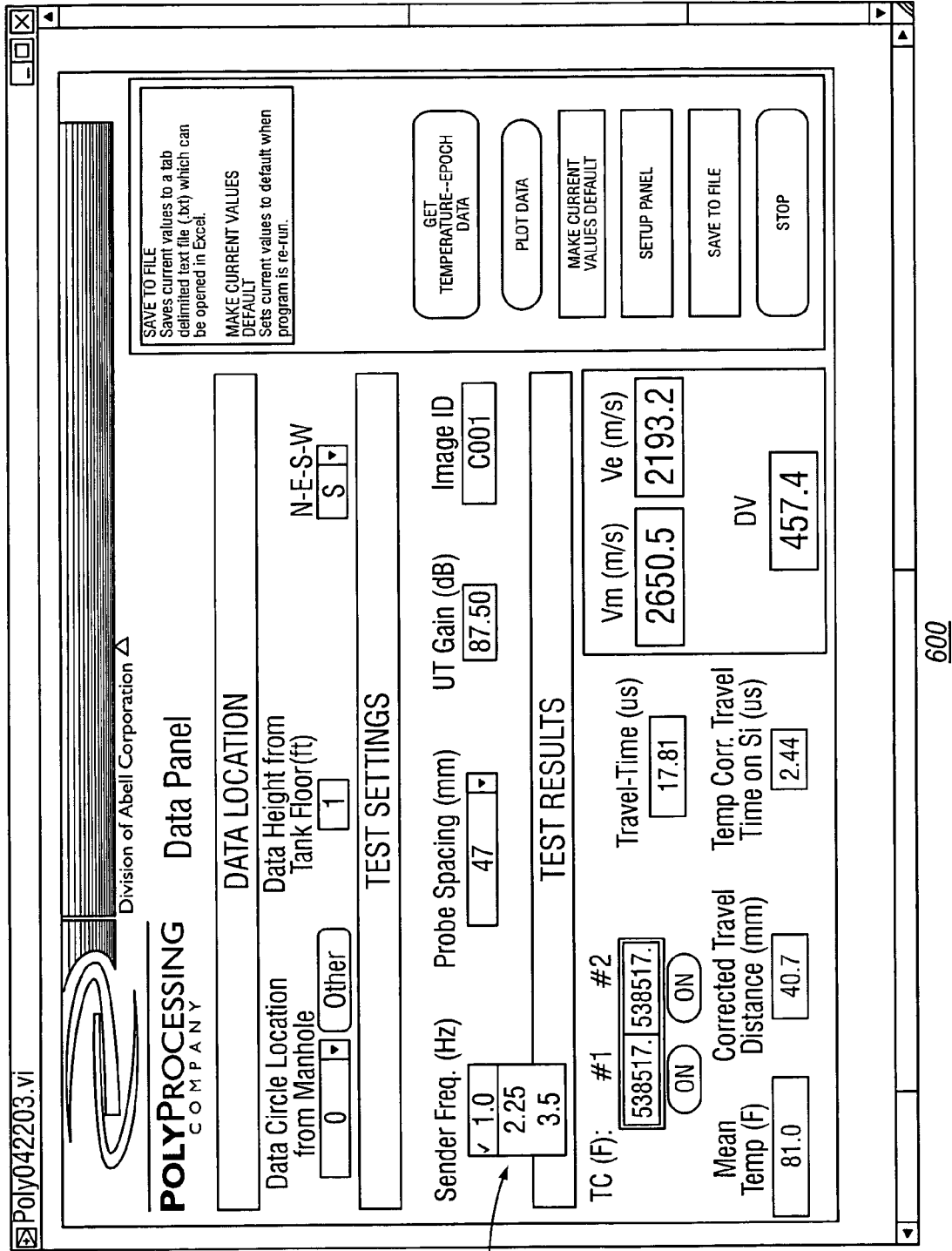
FIG. 6B shows the GUI data panel with the contents of the pull-down menu for the sender frequency used for the ultrasonic analysis.

FIG. 6B shows the GUI data panel 600 with the contents of the pull-down menu 601 for selecting the sender frequency used for the ultrasonic analysis.

Figure 6C:
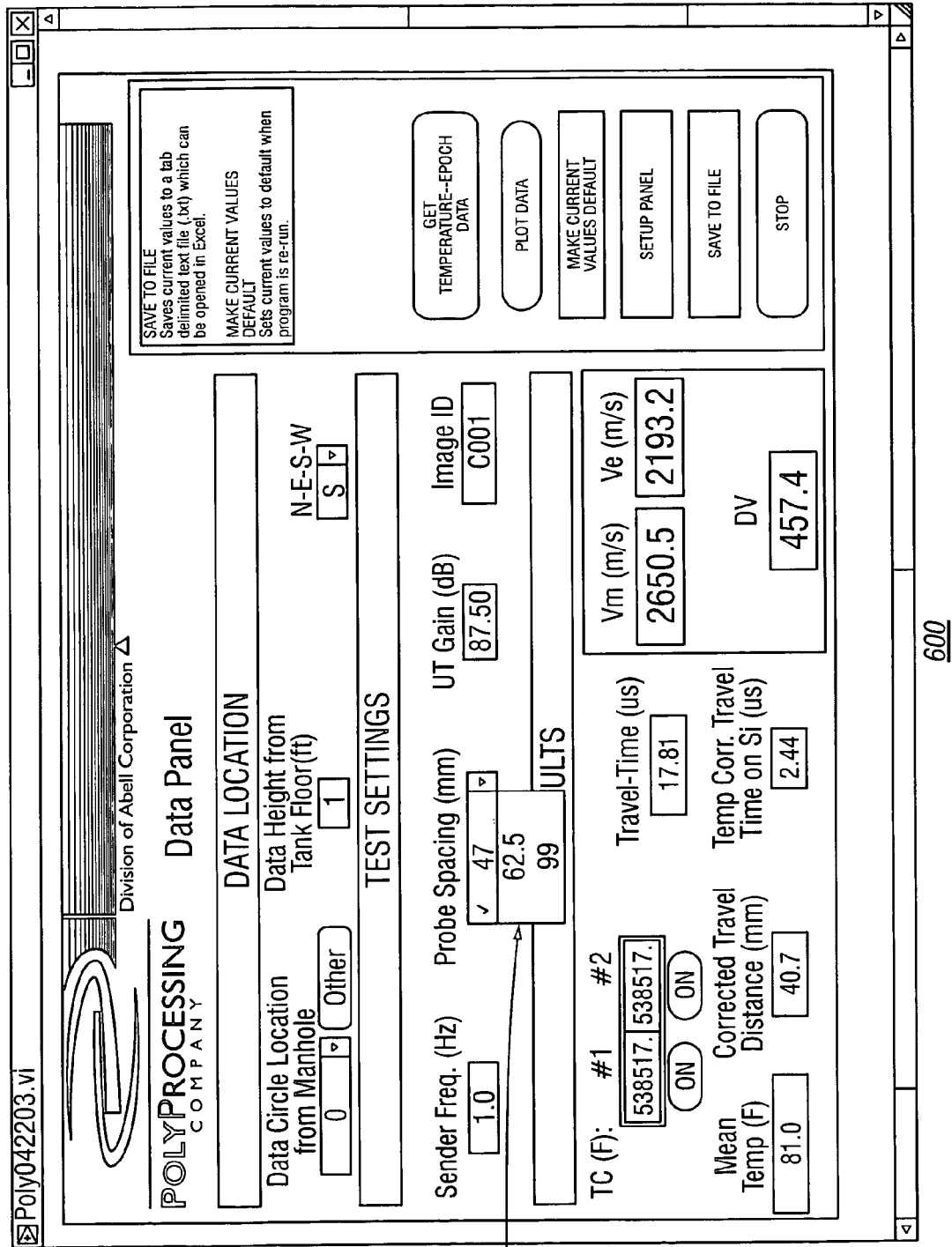
FIG. 6C shows the GUI data panel with the contents of the pull-down menu for the probe spacing.

FIG. 6C shows the GUI data panel 600 with the contents of the pull-down menu 602 for the probe spacing.

The tank temperature is brought into the computer via a PCMIA input card and the LabView software. Correct travel distance for the $L_{CR}$ wave is calculated for each tank and probe combination. The pivot point of the probes is above the entry point of the ultrasonic wave into the tank. For different tank diameters, this entry point will change. This change and the true distance of wave travel is calculated based on input of the probe spacing and tank diameter. This temperature goes to the LabView developed data entry screen, which then calculates the corrected travel distance, the temperature correction, the expected and measured velocity and the difference (ΔV). These values are transferred to an Excel spreadsheet. Tank condition is established based on the velocity difference (ΔV) observed for a particular tank is compared to the prior data stored on an Excel spreadsheet.

The $L_{CR}$ method has been demonstrated in field studies on eleven different rotational molded polyethylene tanks. The tank ages ranged from new to over 25 years. By varying the probe spacing and the frequency to accommodate the increased attenuation in older tanks, velocities obtained from the field showed a distinct and measurable increase age. This velocity increase is consistent with a decrease in fracture toughness for the material. Polymers are known to become more brittle with age, mostly due to ultraviolet degradation.

The description of the present invention has been presented for purposes of illustration and description, and is not intended to be exhaustive or limited to the invention in the form disclosed. Many modifications and variations will be apparent to those of ordinary skill in the art. The embodiment was chosen and described in order to best explain the principles of the invention, the practical application, and to enable others of ordinary skill in the art to understand the invention for various embodiments with various modifications as are suited to the particular use contemplated.

We claim:

1. A system for detecting changes in the properties of a polymeric material, the system comprising:
    a frame held against the outside surface of a curved polymeric test specimen;
    a transmitting probe attached to said frame, wherein the transmitting probe emits critically refracted longitudinal ultrasonic waves that travel across the chord of said curved test specimen;
    at least one receiving probe having a frequency lower than the transmitting probe and attached to said frame, wherein said receiving probe detects said critically refracted ultrasonic waves; and
    a data processing system that measures the travel time of said critically refracted ultrasonic waves from the transmitting probe to the receiving probe and compares said measured travel time to an expected travel time, wherein the speed of said ultrasonic waves is affected by variations in material properties along the penetration path of the ultrasonic waves;
    wherein said transmitting probe and said receiving probe contain silicone cores through which the critically refracted ultrasonic waves travel.

2. The system according to claim 1, further comprising:
    at least one thermocouple attached to said frame that measures the temperature of the surface of said curved polymeric test specimen, wherein said temperature measurement is sent to said data processing system, wherein said measured travel time of the ultrasonic waves is adjusted to account for the effects of temperature.

3. The system according to claim 1, wherein the distance between said transmitting probe and said receiving probe may be adjusted.

4. The system according to claim 1, wherein the frequency of said critically refracted ultrasonic waves may be changed by selecting different transmit/receive combinations, wherein said receiving probe has a lower frequency than said transmitting probe.

5. The system according to claim 1, wherein the curved polymeric test specimen is a container.

6. A method for detecting changes in the properties of a polymeric material, the method comprising:
   holding a frame against the outside surface of a curved polymeric test specimen;
   emitting critically refracted longitudinal ultrasonic waves from a transmitting probe attached to said frame, wherein said waves travel longitudinally across the chord of said curved test specimen;
   detecting said critically refracted longitudinal ultrasonic waves with at least one receiving probe attached to said frame, wherein said receiving probe is of a lower frequency than the transmitting probe; and
   measuring the travel time of said critically refracted ultrasonic waves from the transmitting probe to the receiving probe and comparing said measured travel time to an expected travel time, wherein the speed of said ultrasonic waves is affected by variations in material properties along the penetration path of the ultrasonic waves;
   wherein said transmitting probe and said receiving probe contain silicone cores through which the critically refracted ultrasonic waves travel.

7. The method according to claim 6, wherein the curved polymeric test specimen is a container.

8. The method according to claim 6, further comprising:
   measuring the temperature of the surface of said curved polymeric test specimen with at least one thermocouple attached to said frame; and
   adjusting said measured travel time of the ultrasonic waves to account for the effects of temperature.

9. The method according to claim 6, wherein the distance between said transmitting probe and said receiving probe may be adjusted.

10. The method according to claim 6, wherein the frequency of said critically refracted ultrasonic waves may be changed by selecting different transmit/receive combinations, wherein said receiving probe has a lower frequency than said transmitting probe.

* * * * *